(12) United States Patent
Xie

(10) Patent No.: US 7,888,454 B2
(45) Date of Patent: Feb. 15, 2011

(54) SUBSTITUTED ALDITOL COMPOUNDS, COMPOSITIONS, AND METHODS

(75) Inventor: Chunping Xie, Boiling Springs, SC (US)

(73) Assignee: Milliken & Company, Spartanburg, SC (US)

( * ) Notice: Subject to any disclaimer, the term of this patent is extended or adjusted under 35 U.S.C. 154(b) by 544 days.

(21) Appl. No.: 11/841,271

(22) Filed: Aug. 20, 2007

(65) Prior Publication Data

US 2007/0299256 A1    Dec. 27, 2007

Related U.S. Application Data

(63) Continuation-in-part of application No. 10/831,920, filed on Apr. 26, 2004, now Pat. No. 7,262,236.

(51) Int. Cl.
- C08G 65/34 (2006.01)
- C08G 67/02 (2006.01)
- C08G 61/00 (2006.01)
- C07C 31/18 (2006.01)
- C07C 31/24 (2006.01)

(52) U.S. Cl. ........................ 528/425; 528/392; 528/397; 568/852; 568/853

(58) Field of Classification Search ................ 528/425, 528/392, 397; 568/852, 853
See application file for complete search history.

(56) References Cited

U.S. PATENT DOCUMENTS

| 4,016,118 | A | 4/1977 | Hamada et al. |
| 4,314,039 | A | 2/1982 | Kawai et al. |
| 4,371,645 | A | 2/1983 | Mahaffey, Jr. |
| 4,954,291 | A | 9/1990 | Kobayashi et al. |
| 5,049,605 | A | 9/1991 | Rekers |
| 5,106,999 | A | 4/1992 | Gardlik et al. |
| 5,973,043 | A | 10/1999 | Miley et al. |
| 2005/0239928 | A1 | 10/2005 | Xie et al. |
| 2006/0079720 | A1 | 4/2006 | Xie et al. |

FOREIGN PATENT DOCUMENTS

| JP | 05 117435 A | 5/1993 |
| WO | WO 2005/111134 A2 | 11/2005 |
| WO | WO 2007/127067 A | 11/2007 |

OTHER PUBLICATIONS

Schmid, W. et al, *J. Am. Chem. Soc.* 1991, 113, 6674-6675.
Kim, E. et al. *J. Org. Chem.* 1993, 58, 550-5507.
Higashibayashi, S. et al. *J. Am. Chem. Soc.* 2003, 125, 14379-14393.
Roy, R.B. et al. *J. Org. Chem.* 1971,36, 3242-3243.
Fukase, H. et al. *J. Org. Chem.* 1992, 57, 3642-3650.
Chan, T. H. et al. *Journal of Organic Chemistry* 1999, 64, 4452-4455.
Chaudhuri, Mihir K. et al. *Tetrahedron Letters* 2005, 46, 6247-6251.

*Primary Examiner*—Kriellion A Sanders
(74) *Attorney, Agent, or Firm*—Robert M. Lanning

(57) ABSTRACT

Substituted alditol or carbohydrate compounds having a specified general formula are provided. A method for synthesizing such substituted alditol or carbohydrate compounds is also provided.

8 Claims, No Drawings

SUBSTITUTED ALDITOL COMPOUNDS, COMPOSITIONS, AND METHODS

BACKGROUND OF THE INVENTION

Derivatives of acetals of polyhydric alcohols are useful in several applications, including for example as nucleating agents for polymer resins, and as gelling and thickening agents for organic liquids. Dibenzylidene sorbitol type (DBS) compounds are known for use in such applications.

The use of nucleating agents to reduce the haze in articles manufactured from crystalline polyolefin resins is known in the art. Representative acetals of sorbitol and xylitol, which have been employed as clarifying agents, are described in several patents, including for example: Hamada, et al., U.S. Pat. No. 4,016,118, dibenzylidene sorbitols; Kawai, et al., U.S. Pat. No. 4,314,039, di(alkylbenzylidene) sorbitols; Mahaffey, Jr., U.S. Pat. No. 4,371,645, di-acetals of sorbitol having at least one chlorine or bromine substituent; Kobayashi, et al., U.S. Pat. No. 4,954,291, distribution of diacetals of sorbitol and xylitol made from a mixture of dimethyl or trimethyl substituted benzaldehyde and unsubstituted benzaldehyde. Another reference, U.S. Pat. No. 5,049,605 to Rekers et al. discloses bis(3,4-dialkylbenzylidene) sorbitols, including substituents forming a carbocyclic ring.

Substitution of various groups upon the benzyl ring portion(s) of DBS-based compounds may have a significant impact upon the suitability of such compounds as nucleating or clarifying agents. A significant amount of work in the past has been directed to modifying the substitution of the benzylidene ring substituent(s). However, efforts still are underway to develop other compounds that are likely to afford reduced haze (and corresponding greater clarity) when used as plastic additives in polymer compositions.

The chemical arts often are unpredictable. Changing any portion or substituted group in these particular types of compounds may have a significant impact upon the performance and utility of the compound. This invention recognizes important new compositions that have not been known before, and may be quite useful as plastic additives, or as gelling agents, thickeners, or for other purposes.

DETAILED DESCRIPTION OF THE INVENTION

Reference now will be made to the embodiments of the invention, one or more examples of which are set forth below. Each example is provided by way of explanation of the invention, not as a limitation of the invention. It will be apparent to those skilled in the art that various modifications and variations can be made in this invention without departing from the scope or spirit of the invention.

A polyolefin additive composition is disclosed herein. In some applications, the polyolefin additive composition provides improved transparency to plastic polymer compositions when added to such compositions. In some applications, the additive composition will be advantageous when used in connection with polypropylene, although various applications in connection with other polymers are within the scope of the invention.

Olefin polymers which can be nucleated by such compositions (and whose transparency may be improved according to the practice of the invention) include polymers and copolymers of aliphatic mono-olefins containing from 2 to about 6 carbon atoms, which have an average molecular weight of from about 10,000 to about 2,000,000, preferably from about 30,000 to about 300,000, such as polyethylene, including linear low density polyethylene, low density polyethylene and high density polyethylene, polypropylene, crystalline ethylene/propylene copolymer (random or block), poly(1-butene) and polymethylpentene.

Examples of other thermoplastic polymer resins which may be nucleated with the disclosed acetal compounds include polyester, poly(ethylene terephthalate) (PET) and poly(butylene terephthalate) and polyamide, including nylon 6 and nylon 6,6, poly(phenylene sulfide), syndiotactic polystyrene and polyketones having carbonyl groups in their backbone.

The composition may comprise a polymer selected from aliphatic polyolefins and copolymers containing at least one aliphatic olefin and one or more ethylenically unsaturated comonomers and at least one mono-, di-, or tri-acetal of substituted alditol (such as allyl-sorbitol, propyl-sorbitol, allyl-xylitol, propyl-xylitol and the like).

The mono-, di-, or tri-acetal of substituted alditol may include a composition as described below. For example, and not by way of limitation, a substituted alditol as in Formula (I), which is combined with at least one mole of benzaldehyde selected from the compounds with Formula (II), as shown below.

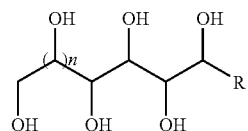

(I)

For Formula (I): n is 0, 1, or 2; and R is independently selected from non-hydrogen groups including alkenyl groups (such as allyl), alkyl groups, including for example alkyl groups having two or more carbons, alkoxy groups, hydroxyl alkyl groups, alkyl-halide groups.

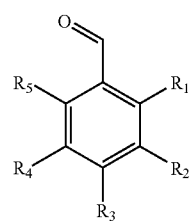

(II)

For Formula (II), $R_1$, $R_2$, $R_3$, $R_4$, and $R_5$ are independently selected from the group consisting of hydrogen, fluorocarbons, alkenyl group, including alkenyl groups having 5 or more carbons, alkyl groups, alkynyl groups, alkoxy groups, carboxy groups, halides, and phenyl, or in some embodiments of the invention, any two adjacent groups may be combined to form a cyclic group, wherein said cyclic group may be comprised of methylenedioxy, cyclopentyl, cyclohexyl, or other similar cyclic groups.

An acetal compound may be formed in one particular embodiment of the invention by the process of: (a) reacting a polyhydric alcohol with an alkenyl molecule to form a first compound; and (b) reacting in a condensation reaction said first compound with an aromatic aldehyde to form an acetal compound. However, the invention may be practiced in other ways as well. The acetal compound thus formed may be a mono-, di-, or tri-acetal, but in many cases it has been found that a di-acetal is particularly useful. The acetal compound may comprise an allyl in one particular embodiment of the invention, as herein further described.

In some applications, such a reaction product or resulting composition is a di-acetal (and thus the result of a 1:2 molar ratio reaction between the alditol and benzaldehyde). A composition may be provided having the structure of Formula (III), below. A single acetal, or a triacetal, could also be provided in the practice of the invention, but one particular di-acetal composition is shown below:

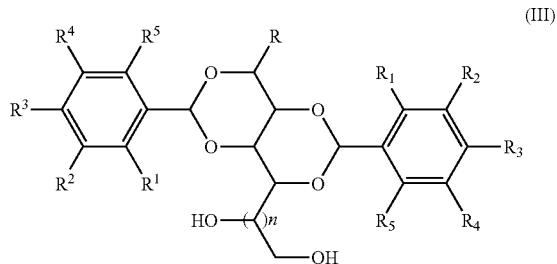

(III)

In the composition, n may be 0, 1, or 2; and $R_1$, $R_2$, $R_3$, $R_4$, and $R_5$ can be the same groups as those defined above for Formula (II). Furthermore, R may be selected from the group consisting of: alkenyls, alkyls having two or more carbons, three carbon alkyls (i.e. n-propyl), four carbon alkyls (butyl), alkoxy, hydroxyl alkyls, and alkyl-halides. R may comprise an alkenyl, and in some particular embodiments of the invention, an allyl has been found to work quite well for the R group.

It should be appreciated that the R group stereochemistry is not defined, and the invention is not limited to any particular R group stereochemistry, such that all chemical structures provided herein shall cover any isomers that occur due to stereoisomers of the carbon atom to which R is attached. The carbon to which the R group is attached is sometimes referred to herein as the C-1 carbon.

It should be appreciated with regard to the composition set forth above that while only the 1,3; 2:4 isomer is represented (i.e. the numbered carbons on the sorbitol chain which form the two acetals), this structure is provided for convenience and illustration only and the invention is not limited to only isomers of the 1,3:2,4 type, but may include any and all other isomers as well, including also isomers of the 1:3; 4:6 and 2, 4:3,5 type, as examples.

The diacetals, triacetals, and monoacetals of the invention may be condensation products of substituted alditols, such as (but not limited to) allyl-sorbitol, propyl-sorbitol, 1-methyl-2-propenyl sorbitol, allyl-xylitol, propyl-xylitol, and a (substituted) benzaldehyde. Examples of suitable (substituted) benzaldehydes include benzaldehyde, 4-ethylbenzaldehyde, 4-isobutylbenzaldehyde, 4-fluoro-3-methylbenzaldehyde, 5,6,7,8-tetrahydro-2-naphthaldehydebenzylidene, 3-methylbenzaldehyde, 4-propylbenzaldehyde, 4-butylbenzaldehyde, 4-methoxybenzaldehyde, 3-chlorobenzaldehyde, 3,4-dimethylbenzaldehyde, 3,5-difluorobenzaldehyde, 3-fluorobenzaldehyde, 4-fluorobenzaldehyde, 3-bromo-4-fluorobenzaldehyde, 3-methyl-4-methoxybenzaldehyde, 2,4,5-trimethylbenzaldehyde, 4-chloro-3-fluorobenzaldehyde, 4-methylbenzaldehyde, 3-bromobenzaldehyde, 4-methoxybenzaldehyde, 3,4-dichlorobenzaldehyde, 4-fluoro-3,5-dimethylbenzaldehyde, 2,4-dimethylbenzaldehyde, 4-bromobenzaldehyde, 3-ethoxybenzaldehyde, 4-allyloxybenzaldehyde, 3,5-dimethylbenzaldehyde, 4-chlorobenzaldehyde, 3-methoxybenzaldehyde, 4-(trifluoromethyl)benzaldehyde, 2-naphthaldehyde, 4-isopropylbenzaldehyde, 3,4-diethoxybenzaldehyde, 3-bromo-4-ethoxybenzaldehyde, piperonal, 3,4-dimethoxybenzaldehyde, 4-carboxybenzaldehyde, 3-hex-1-ynylbenzaldehyde, and 2-chlorobenzaldehyde. Preferred di-acetals of the present invention include 1, 3:2,4-bis(4-ethylbenzylidene)-1-allyl-sorbitol, 1,3,2,4-bis(3'-methyl-4'-fluoro-benzylidene)-1-propyl-sorbitol, 1,3,2,4-bis(5',6',7',8'-tetrahydro-2-naphthaldehydebenzylidene)-1-allyl-xylitol, bis-1,3,2-4-(3',4'-dimethylbenzylidene)-1"-methyl-2"-propyl-sorbitol, 1,3,2,4-bis(3',4'-dimethylbenzylidene)-1-propyl-xylitol.

The di-acetals and mono-acetals of the present invention may be prepared by a variety of techniques, some of which are known in the art. Generally, such procedures employ the reaction of one mole of substituted alditol (such as allyl-sorbitol, propyl-sorbitol, allyl-xylitol, propyl-xylitol and the like) with 2 moles of aldehyde (for diacetals), with 1 mole of aldehyde (for monoacetals), or with 3 moles of aldehyde (for triacetals) in the presence of an acid catalyst (inorganic acid such as hydrochloric acid or organic acid such as p-toluenesulfonic acid (pTSA)). Further, an organic solvent is employed that is miscible with water (such as low alkyl alcohols, N—N-dimethylformamide, or acetic acid) at room temperature.

One method that can be employed to prepare di-acetals of the invention is described in U.S. Pat. No. 5,106,999 to Gardlik et al., which is hereby incorporated by reference.

Methods to prepare and synthesize the carbohydrates of varying chain length are disclosed in Kim, Gordon, Schmid, and Whitesides, *Tin and Indium Mediated Allylation in Aqueous Media: Application to Unprotected Carbohydrates*, J. Org. Chem., 5500-5507, 58 (1993) and in Whiteside, *Journal of the American Chemical Society*, 113, 6674-6675 (1991). Whiteside has suggested the reaction of glucose with allyl bromide/tin.

One reaction method that may be employed in the preparing starting materials for the synthesis of compositions needed in the practice of the invention are shown below, in which an allyl group may be added to a carbohydrate. The reaction scheme illustrated is merely one example, and similar reactions can be carried out for carbohydrates having more or less carbon groups in the chain.

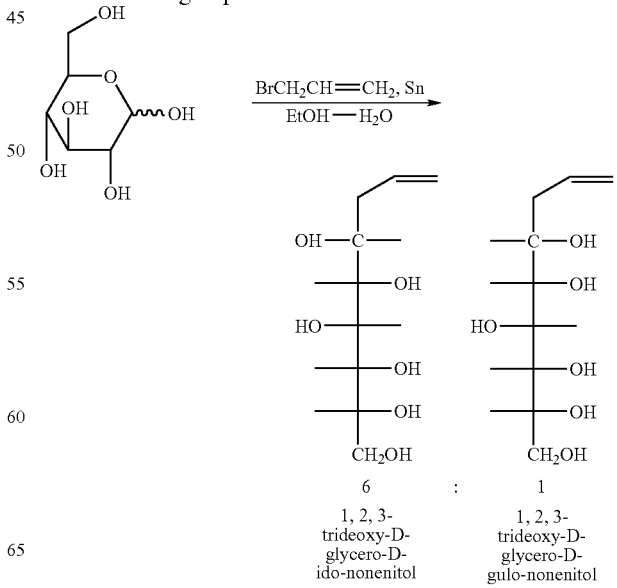

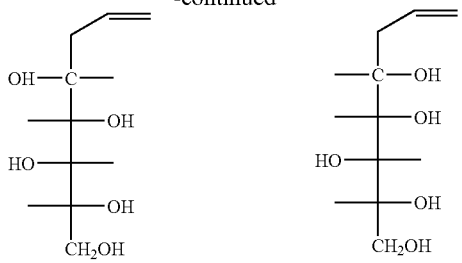

1, 2, 3-trideoxy-D-ido-D-ido-octenitol    1, 2, 3-trideoxy-D-gulo-octenitol

In the practice of the invention, an acetal compound formed by the process of: (a) reacting a polyhydric alcohol and an alkenyl or alkyl group to form a first compound; and (b) reacting in a condensation reaction said first compound with an aromatic aldehyde to form an acetal compound. In some particular applications of the invention, the alkenyl group comprises an allyl.

It has been discovered in the course of work leading to one embodiment of the invention herein that allyl bromide/tin chemistry as illustrated above is one manner of synthesis for a carbohydrate hydrocarbon chain that can be used as one step in a sequence of reactions to unexpectedly provide significant advantages and valuable compositions. This general reaction pathway may be used in various forms to synthesize carbohydrates in the manufacture of the compositions of the invention. One embodiment of the invention relates to the use of carbohydrate synthesis reactions in combination with other acetal formation reactions to prepare compositions of the invention.

Substituted sorbitol diacetals, triacetals, and monoacetals may be prepared. These structures contain mixtures of any correlated types of acetals (such as the related di-, tri-, and/or mono-acetals of the target acetal). Although it may not always be necessary to remove these impurities (particularly if they are present in very low proportions) prior to incorporation of the di-acetal, triacetal or monoacetal into the target polyolefin, it may be desirable to do so and such purification may serve to enhance the transparency of the resin produced. This optional purification step may be accomplished by using a reducing agent.

Purification of a di-acetal may be accomplished, in one embodiment of the invention, by removal of any present tri-acetals by the extraction thereof with a relatively non-polar solvent, or reducing agent. As one non-limited example, by removal of the impurities, the product may be purified so that the amount of di-acetal in the additive composition contains at least about 95 percent and even up to 98 percent di-acetal or more, depending upon the application.

A more complete synthesis pathway is shown below, which is merely illustrative, and not limited to only those species or reactions shown:

Synthesis Pathway(s)

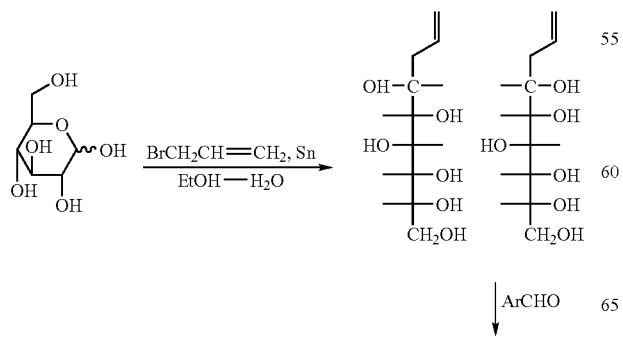

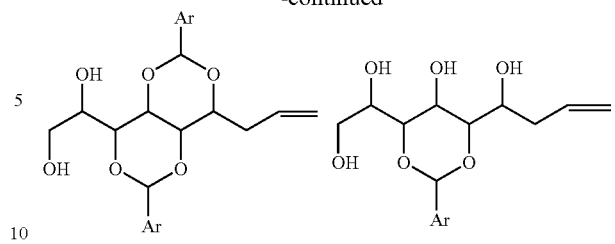

Generic Structure of a Synthesized Acetal-Based Composition

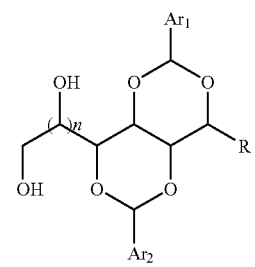

Many different substituted benzyl groups may be employed for $Ar_1$ and $Ar_2$ in the practice of the invention, as shown by several representative examples in Table 1, which were synthesized and tested as shown in the Examples listed herein. Substituted groups for $Ar_1$ and/or $Ar_2$ are not limited to only those found in Table 1. For example, Table 1 reports various compositions for which n=0 and where n=1 for various substituted $Ar_1$ and $Ar_2$ groups. When n=0, the xylitol moity is employed. When n=1, the sorbitol moity is employed. Although n=2 compounds are not reported in Table 1, such compounds are within the scope of the invention, and are within the teachings provided herein. There is no practical limit to what may be substituted in such compositions, so long as they are chemically possible. However, it has been found that certain substituted groups on this compound provide enhanced properties.

In the practice of the invention, R may be selected from a wide variety of compounds, including without limitation and by way of example:

—$CH_3$; —$CH_2CH_3$;

—$CH_2CH_2CH_3$; —$CH_2CH_2CH_2CH_3$;

—$CH_2CH=CH_2$; —$CH(CH_3)CH=CH_2$;

—$CH_2CH$—X—$CH_2$—X'; —$CH_2CH_2$—X''—$CH_2$—$CH_3$;

—$CH_2CH$—X'''—$CH_2OH$; —CH—OH—CH—OH—$CH_2$—OH.

With regard to the compounds above, X, X', X", and X'" comprise independently selected halide groups in those selected compounds, if they are employed.

The allyl species (—$CH_2CH=CH_2$) is sometimes particularly advantageous, and several such species were synthesized and reported along with others in Table 1 herein.

TABLE 1

Substitution of Groups with Corresponding Melting Points

| Example Reported Herein | n | R | Ar₁, Ar₂ | Melting Point (° C.) |
|---|---|---|---|---|
| 2 | 1 | —CH$_2$CH=CH$_2$ | 4-ethylphenyl (—C₆H₄—C₂H₅) | 244-246 |
| 3 | 1 | —CH$_2$CH=CH$_2$ | 2-methyl-4-methoxyphenyl (with CH₃ and OCH₃) | 237-239 |
| 4 | 1 | —CH$_2$CH=CH$_2$ | 3,4-dichlorophenyl | 275-280 |
| 5 | 1 | —CH$_2$CH=CH$_2$ | 3-methylphenyl with isopropylethynyl substituent | 190-192 |
| 6 | 1 | —CH$_2$CH=CH$_2$ | 4-(COOCH$_3$)phenyl | 295-300 |
| 7 | 1 | —CH$_2$CH=CH$_2$ | naphthyl | 247-249 |
| 8 | 1 | —CH$_2$CH=CH$_2$ | 2,6-dimethyl-3-fluorophenyl | 286-288 |
| 10 | 0 | —CH$_2$CH=CH$_2$ | 5,6,7,8-tetrahydronaphthyl | 210-212 |
| 11 | 0 | —CH$_2$CH=CH$_2$ | trimethylphenyl (2,4,5-trimethyl) | 274-276 |
| 12 | 0 | —CH$_2$CH=CH$_2$ | benzo[1,3]dioxolyl | 217-219 |

TABLE 1-continued

Substitution of Groups with Corresponding Melting Points

| Example Reported Herein | n | R | Ar$_1$, Ar$_2$ | Melting Point (° C.) |
|---|---|---|---|---|
| 13 | 0 | —CH$_2$CH$_2$CH$_3$ | 2,3-dimethylphenyl | 255-257 |
| 14 | 1 | —CH$_2$CH$_2$CH$_3$ | 3-methyl-4-fluorophenyl | 252-254 |
| 15 | 1 | —CH(CH$_3$)CH=CH$_2$ | 3,4-dimethylphenyl | 233-235 |
| 16 | 1 | —CH$_2$CHBrCH$_2$Br (90%)<br>—CH$_2$CHBrCH$_2$OH (10%) | phenyl | 188-190 |
| 17 | 1 | —CH$_2$CH=CH$_2$ | Ar$_1$ = 4-methylphenyl; Ar$_2$ = 3,4-dimethylphenyl | 234-236 |

EXAMPLE 1

1-Allyl Sorbitol

A three liter three-necked round bottom flask, equipped with heating mantle, stirrer, nitrogen inlet, and condensor, was charged with 900 mL of ethanol, 150 mL of water, 180 g (1.00 mole) of D-glucose, 119 g (1.00 mole) of tin powder (−100 mesh), and 121 g (1.00 mole) of allyl bromide. The mixture was stirred and slowly heated to reflux—a significant exotherm and gas evolution was observed at 60° C. The gray suspension was stirred at reflux for two days, in which time the reaction mixture turned an orange/brown color. Heat was removed and the mixture was allowed to cool to room temperature. The reaction was neutralized to pH=7 by adding approximately 200 ml of 5M NaOH aqueous solution. The suspension was filtered to remove solids, and the yellow solution was decolorized with multiple treatments of activated carbon. The activated carbon was removed by filtration, and the solvent was removed by rotary evaporation to isolate a white syrup. Typical yield was 200 g with threo-erythro ratio of 7:1, based on GC-MS. The syrup was used without further purification.

Pure threo isomer could be obtained by hydrolysis of any of the example 2-8. $^1$H NMR (500 MHz, D$_2$O, ppm): 2.34-2.37 (m, 2H), 3.63-3.95 (m, 7H), 5.13-5.20 (m, 2H), 5.88-5.89 (m, 1H). $^{13}$C NMR (125 MHz, D$_2$O, ppm): 38.32, 63.69, 70.74, 71.14, 71.80, 71.92, 74.58, 118.60, 135.72.

EXAMPLE 2

Bis-1,3,2,4-(4'-ethylbenzylidene)-1-Ally Sorbitol

A two liter reaction kettle, equipped with a stirrer and nitrogen inlet, was charged with 111 g (0.50 mol) of 1-allyl sorbitol syrup (product of example 1) in 100 mL of 6N HCl solution. 134 g (1.0 mol) of 4-ethylbenzaldehyde in 800 mL of methanol was added to the reaction vessel. The clear solution was stirred for 48 hours, during which time a significant amount of white precipitate formed. The powder was isolated by filtration and washed with 250 ml of 1 M NaOH aqueous solution. The powder was suspended in water and further neutralized to pH=7 with a small amount of NaOH. The suspension was heated to boiling, then filtered. The white powder was washed with 7×500 ml of boiling water. The washed powder dried overnight. The powder was then stirred in 500 mL of cyclohexane, heated until boiling, filtered, and washed with 2×250 ml of boiling cyclohexane. The isolated white powder was dried in a vacuum oven to give 107 g of product, m.p. 244-246° C. The purity was above 99%, based on GC-MS. 1H NMR (300 MHz, DMSO-d6, ppm): 1.14-1.19 (t, 6H), 2.39-2.44 (t, 2H), 2.56-2.63 (q, 4H), 3.41-4.10 (m, 7H), 4.38-4.42 (t, 1H), 4.81-4.83 (d, 1H), 5.07-5.19 (q, 2H), 5.60-5.64 (d, 2H), 5.84-5.89 (m, 1H), 7.19-7.23 (t, 4H), 7.34-7.38 (t, 4H).

EXAMPLES 3-8

A variety of allyl-substituted dibenzylidene-based (DBS) molecules were synthesized using the procedures similar to the one described in Example 2 above. Structures are shown in Table I, with measured values for melting point. All derivatives had NMR consistent with the indicated structures, and purities of at least 95%, based on GC-MS.

EXAMPLE 9

1-Allyl Xylitol

A five liter three-necked round bottom flask, equipped with heating mantle, stirrer, nitrogen inlet, and condenser, was charged with 1.8 liters of ethanol, 0.3 liters of water, 300 g (2.00 mole) of D-xylose, 242 g (2.04 mole) of tin powder (−325 mesh), and 242 g (2.00 mole) of allyl bromide. The mixture was stirred and slowly heated to reflux—a significant exotherm and gas evolution was observed at 60° C. The gray suspension was stirred at reflux for three days, in which time the reaction mixture turned an orange/brown color. Heat was removed and the mixture was allowed to cool to room temperature. The reaction was neutralized to pH=7 by adding approximately 400 ml of 5M NaOH aqueous solution. The suspension was filtered to remove solids, and the yellow solution was decolorized with multiple treatments of activated carbon. The activated carbon was removed by filtration, and the solvent was removed by rotary evaporation to isolate a white syrup. Typical yield was 320 g. 1H NMR (300 MHz, $D_2O$, ppm): 2.33-2.39 (m, 2H), 3.55-3.89 (m, 6H), 5.14-5.23 (m, 2H), 5.89 (m, 1H). The syrup was used without further purification.

EXAMPLE 10

Bis-1,3,2,4-(5',6',7',8'-tetrahydro-2-naphthaldehyde-benzylidene) 1-Allyl Xylitol A two liter reaction kettle, equipped with a stirrer and nitrogen inlet, was charged with 144 g (0.75 mol) of 1-allyl xylitol syrup (product of example 9), 300 mL of water, and 100 mL of concentrated (12N)HCl. The mixture was stirred until the 1-allyl xylitol had completely dissolved. 240 g (1.50 mol) of 5',6',7',8'-tetrahydro-2-naphthaldehyde in 400 mL of methanol was added to the reaction vessel. The solution was stirred for two days, during which time a significant amount of white precipitate formed. The powder was isolated by filtration and washed with 250 ml of 1 M NaOH aqueous solution. The powder was suspended in water and further neutralized to pH=8 with a small amount of NaOH. The suspension was heated to boiling, then filtered. The white powder was washed with 7×500 ml of boiling water. The washed powder dried overnight. The powder was then stirred in 0.5 liters of cyclohexane, heated until boiling, filtered, and washed with 2×250 ml of boiling cyclohexane. The isolated white powder was dried in a vacuum oven, to give 47.8 g of product, m.p. 210-212° C. The purity was 99%, based on GC-MS. 1H NMR (300 MHz, DMSO-d6, ppm): 1.72 (m, 8H), 2.36-2.51 (t, 2H), 2.71 (m, 8H), 3.54-4.03 (m, 6H), 4.76-4.80 (t, 1H), 5.07-5.17 (q, 2H), 5.56-5.77 (d, 2H), 5.80-5.90 (m, 1H), 7.02-7.06 (m, 2H), 7.11-7.17 (m, 4H).

EXAMPLE 11, 12

A variety of allyl DBXs were synthesized using the procedure similar to the one described in Example 2. The structures of example 10 and 11 are shown in Table 1. All derivatives had NMR consistent with the indicated structures, and purities of at least 95%, based on GC-MS.

EXAMPLE 13

Bis-1,3:2,4-(3',4'-Dimethylbenzylidene)-1-Propyl Xylitol 58 g (0.3 mol) of 1-allyl xylitol syrup (example 8) was dissolved in 60 ml water. About 0.6 g of platinum (5% weight on activated carbon) was added and the mixture was hydrogenated at room temperature with hydrogen pressure at 60 psi. The reaction was stopped until no hydrogen pressure drop was observed. The solid was filtered. The allyl group of the solution was completely turned into propyl group based on NMR. 100 g (0.6 mol) of 3,4-dimethyl benzaldehyde, 500 ml ethanol, and 50 mL concentrated HCl (12N) were added into the sugar solution. The clear solution was stirred at room temperature overnight, during which time a significant amount of white precipitate formed. The powder was isolated by filtration and washed with 100 ml of 1 M NaOH aqueous solution. The powder was suspended in water and further neutralized to pH=7 with a small amount of NaOH. The suspension was heated to boiling, then filtered. The white powder was washed with 7×500 ml of boiling water. The washed powder dried overnight. The powder was then stirred in 500 mL of cyclohexane, heated until boiling, filtered, and washed with 2×250 ml of boiling cyclohexane. The isolated white powder was washed with methanol, dried in a vacuum oven to give 21 g of product, m.p. 255-257° C. The purity was above 98%, based on GC-MS. 1H NMR (300 MHz, DMSO-d6, ppm): 0.89-0.93 (t, 3H), 1.30-1.50 (m, 2H), 1.50-1.70 (m, 2H), 2.22 (12H), 3.50-4.05 (m, 6H), 4.78 (1H), 5.56-5.59 (d, 2H), 7.14-7.21 (m, 6H).

EXAMPLE 14

Bis-1,3,2,4-(3'-methyl-4'-fluoro-benzylidene) 1-Propyl Sorbitol

About 85 g (0.38 mol) of 1-allyl sorbitol syrup (product of example 1) was dissolved in 85 ml water. 0.8 g of platinum (5% weight on activated carbon) was added and the mixture was hydrogenated at room temperature with hydrogen pressure at 60 psi. The reaction was stopped until no hydrogen pressure drop was observed. The solid was filtered. The allyl group of the solution was completely turned into propyl group based on NMR.

Pure threo isomer could be separated from 2-propanol recrystallization. White needle crystal with melting point of 119-120° C. 1H NMR (500 MHz, $D_2O$, ppm): 0.92-0.95 (t, 3H), 1.36-1.47 (m, 2H), 1.53-1.57 (m, 2H), 3.65-3.69 (m, 2H), 3.72-3.74 (dd, 1H), 3.77-3.82 (m, 2H), 3.83-3.86 (dd, 1H), 3.95-3.97 (dd, 1H). $^{13}C$ NMR (125 MHz, $D_2O$, ppm): 13.40, 18.51, 35.00, 63.05, 70.21, 70.86, 71.26, 71.29, 74.53.

75 g (0.54 mol) of 3-methyl-4-fluoro benzaldehyde, 500 ml ethanol, and 56 mL concentrated HCl (12N) were added into the sugar solution. The clear solution was stirred at room temperature overnight, during which time a significant amount of white precipitate formed. The powder was isolated by filtration and washed with 100 ml of 1 M NaOH aqueous solution. The powder was suspended in water and further neutralized to pH=7 with a small amount of NaOH. The suspension was heated to boiling, then filtered. The white powder was washed with 7×500 ml of boiling water. The washed powder dried overnight. The powder was then stirred in 500 mL of cyclohexane, heated until boiling, filtered, and washed with 2×250 ml of boiling cyclohexane. The isolated white powder was washed with methanol, dried in a vacuum oven to give 21 g of product, m.p. 253° C. The purity was above 98%, based on GC-MS. 1H NMR (300 MHz, DMSO-$d_6$, ppm): 0.91-0.95 (t, 3H), 1.40-1.48 (m, 2H), 1.54-1.67 (m, 2H), 2.13-2.25 (6H), 3.42-4.05 (m, 7H), 4.40 (t, 1H), 4.82-4.84 (d, 1H), 5.60-5.62 (d, 2H), 7.11-7.16 (m, 2H), 7.30-7.37 (m, 4H).

EXAMPLE 15

Bis-1,3,2-4-(3',4'-Dimethylbenzylidene) 1'-Methyl-2'-PropenylSorbitol

A two liter three-necked round bottom flask, equipped with heating mantle, stirrer, nitrogen inlet, and a condensor, was charged with 600 mL of ethanol, 100 mL of water, 126 g (0.70 mole) of D-glucose, 84 g (0.7 mole) of tin powder (−100 mesh), and 131 g (0.97 mole) of crotyl bromide. The mixture was stirred and slowly heated to reflux—a significant exotherm and gas evolution was observed at 60° C. The gray suspension was stirred at reflux overnight, in which time the reaction mixture turned light yellow. Heat was removed and the mixture was allowed to cool to room temperature. The reaction was filtrated and the solution was stirred with 188 g (1.4 mol) 3,4-dimethyl benzaldehyde overnight, during which time a significant amount of precipitate formed. The yellow solid was isolated by filtration, washed with methanol to give a white powder, m.p. 233-235° C. GC-MS and NMR indicated the desired compound as a mixture of two diastereomers (2:1), of 1-methyl-2-propenyl.

EXAMPLE 16

Bis-1,3,2,4-Dibenzylidene 2',3'-Dibromopropyl Sorbitol/Bis-1,3,2,4-Dibenzylidene 2'-Bromo-3'-Hydroxypropyl Sorbitol An aqueous solution of 90 g allyl sorbitol syrup (example 1) in 110 g of methanol was titrated with bromine until a light yellow solution. Small amount of NaHSO3 was added to give a colorless solution. 1.9 g of p-toulenesulfonic acid monohydrate was added. The clear solution was stirred overnight, during which time a significant amount of white precipitate formed. The powder was isolated by filtration and washed with 1 M NaOH aqueous solution. The powder was suspended in water and further neutralized to pH=7 with a small amount of NaOH. The suspension was heated to boiling, then filtered. The white powder was washed with 7×500 ml of boiling water. The washed powder dried overnight. The powder was then stirred in 50 mL of cyclohexane, heated until boiling, filtered, and washed with 2×25 ml of boiling cyclohexane. The product was dried in a vacuum oven to give 7.3 g of white powder, m.p. 188-190° C. GC-MS and NMR indicated a mixture of bis-1,3,2,4-dibenzylidene 2',3'-dibromopropyl sorbitol (90%) and bis-1,3,2,4-dibenzylidene 2'-bromo-3'-hydroxypropyl sorbitol (10%).

EXAMPLE 17

Asymmetric benzylidene/2,4-dimethylbenzylidene 1-Allyl Sorbitol

A two liter reaction kettle, equipped with a stirrer and nitrogen inlet, was charged with 111 g (0.50 mol) of 1-allyl sorbitol syrup (product of example 1) in 280 ml methanol solution. 9.5 g of PTSA, 53 g (0.5 mol) of benzaldehyde and 67 g (0.50 mol) of 2,4-dimethylbenzaldehyde were added to the reaction vessel. The clear solution was stirred for 48 hours, during which time a significant amount of white precipitate formed. The powder was isolated by filtration and washed with 250 ml of 1 M NaOH aqueous solution. The powder was suspended in water and further neutralized to pH=7 with a small amount of NaOH. The suspension was heated to boiling, then filtered. The white powder was washed with 7×500 ml of boiling water. The washed powder dried overnight. The powder was then stirred in 500 mL of cyclohexane, heated until boiling, filtered, and washed with 2×250 ml of boiling cyclohexane. The isolated white powder was dried in a vacuum oven to give 38.4 g of product, m.p. 234-236° C. Standard analyses of the material indicated that it consisted of a mixture of 1,3-O-(benzylidene):2,4-O-(2,4-dimethylbenzylidene) 1-allyl sorbitol and 1,3-O-(2,4-dimethylbenzylidene) 1-allyl sorbitol (85%), 1, 3:2,4-bis(benzylidene) 1-allyl sorbitol (5%) and 1, 3:2,4-bis(2,4-dimethylbenzylidene) 1-allyl sorbitol (10%).

EXAMPLE 18

Compositions containing various levels of the acetal of examples 2-16, coadditives (0.05 wt. % Irganox 1010, 0.1 wt. % Irgafos 168, and 0.08 wt. % calcium stearate) and the balance polypropylene homopolymer or polypropene random copolymer (3% ethylene content) were dry blended in a mechanical mixer, extruded through a single screw extruder at 240° C. and pelletized. Plaques were prepared (1.27 mm thick) by injection molding the pellets at 220° C.

The Tc and haze were measured, and the results are reported in Table 2. Millad 3988® is a registered trademark of Milliken and Company of Spartanburg, S.C. Millad 3988® is a commercially distributed clarifying agent product that employs bis(3,4-dimethylbenzylidene sorbitol)("DMDBS"), as shown and described in U.S. Pat. No. 5,049,605.

TABLE 2

Percent Haze Measurements for Various Compounds

| Polymer | Example | Concentration (ppm) | Tc (° C.) | Haze(%) |
|---|---|---|---|---|
| RCP PP | (Control) | — | 101.2 | 44.3 |
| RCP PP | Millad 3988 ® | 2500 | 113.6 | 7.2 |
| RCP PP | 2 | 6000 | 115.1 | 4.9 |
| RCP PP | 3 | 3500 | 109.4 | 8.8 |
| RCP PP | 4 | 5000 | 113.1 | 10.5 |
| RCP PP | 5 | 5000 | 107.8 | 17.2 |
| RCP PP | 6 | 2000 | 105.2 | 23.3 |
| RCP PP | 8 | 5000 | 109.0 | 8.9 |
| RCP PP | 10 | 5000 | 109.6 | 11.3 |
| RCP PP | 11 | 5000 | 111.9 | 21.8 |
| RCP PP | 12 | 5000 | 110.8 | 19.9 |
| RCP PP | 13 | 5000 | 109.5 | 8.4 |
| RCP PP | 14 | 5000 | 111.5 | 5.6 |
| RCP PP | 15 | 5000 | 105.8 | 8.8 |
| RCP PP | 16 | 3000 | 107.0 | 18.9 |
| PP | (Control) | — | 116.6 | 58.1 |
| PP | Millad 3988 | 2500 | 124.0 | 11.7 |
| PP | 2 | 5000 | 125.2 | 7.5 |

In some applications of the invention, the nucleating agent composition may be added to the polymer resin at a concentration of from about 0.005 to about 3 weight percent. In other applications, a concentration of between about 0.01 and about 1 weight percent may be employed. In other applications, a concentration of between about 0.025 and about 0.5 weight percent of the composition is useful.

Concentrates of up to 50 weight percent of the nucleating agent in resin may also be prepared for blending with additional resin prior to molding. Typically, concentrates containing 33 weight percent or less of the nucleating agent in resin are used commercially.

The resin may be extruded a second time immediately before being processed into a finished article by, for example, injection molding, extrusion blow molding, injection blow molding, stretch blow molding, compression molding, rotational molding, profile extrusion, sheet extrusion, thermal forming, film extrusion, and film extrusion with orientation.

Gel Formation and Testing

Solid gels also were produced comprising the inventive substituted-alditol derivatives through recognized, simple methods. In particular, specific organic solvents were combined with the additives in certain concentrations and mixed thoroughly. The resultant mixture was then heated to a temperature between about 170° F. (77° C.) and 300° F. (149° C.), as indicated below, under agitation for between 5 and 120 minutes. The resultant solution was then poured into a mold to produce a gel stick. The solvents listed are not intended to be exhaustive as to the potential types which may be utilized to form gels with the inventive substituted-alditol derivatives, and thus are merely listed as preferred solvents for such purposes. The examples below were analyzed empirically and by touch to determine if a gel actually formed and the hardness properties as well as any formed gels. Results are reported in Table 3.

TABLE 3

Gel Sample Data

| Sample Number | SOLVENT | ADDITIVE (Example # above) | DBS Conc. (Weight %) | Gel Formation (Y/N) | Gel Character (Hard/Soft) |
|---|---|---|---|---|---|
| 1 | 1,2-Propanediol | 2 | 1 | Y | Hard |
| 2 | 1,3-Propanediol | 2 | 1 | Y | Hard |
| 3 | 2-Chlorotoluene | 2 | 1 | Y | Soft |
| 4 | Toluene | 2 | 1 | Y | Soft |
| 5 | Benzonitrile | 2 | 1 | Y | Soft |
| 6 | 1,2-Propanediol | 13 | 1 | Y | Hard |
| 7 | 2-Chlorotoluene | 13 | 1 | Y | Hard |
| 8 | Benzonitrile | 2 | 3 | Y | Hard |
| 9 | 1,2-Propanediol | 2 | 3 | Y | Hard |
| 10 | 1,3-Propanediol | 2 | 3 | Y | Hard |
| 11 | 2-Chlorotoluene | 2 | 3 | Y | Soft |
| 12 | 1,2-Propanediol | 13 | 3 | Y | Hard |
| 13 | 2-Chlorotoluene | 13 | 3 | Y | Hard |

Thus, the inventive substituted-alditol derivatives provide excellent gelling capabilities for solvents, depending upon their concentration without the target solvents.

It is understood by one of ordinary skill in the art that the present discussion is a description of exemplary embodiments only, and is not intended as limiting the broader aspects of the present invention, which broader aspects are embodied in the exemplary constructions. The invention is shown by example in the appended claims.

The invention claimed is:

1. A compound having the general formula:

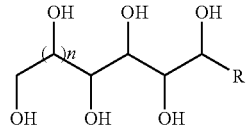

wherein n is 0, 1, or 2;
R is independently selected from the group consisting of alkoxy groups, hydroxyl alkyls, and alkyl-halides, and the hydroxyl alkyls are selected from the group consisting of —$CH_2CHX'''CH_2OH$ and —$CHOHCHOHCH_2OH$, where X''' is a halide.

2. The compound of claim 1, wherein n is 0.
3. The compound of claim 1, wherein n is 1.
4. The compound of claim 1, wherein n is 2.
5. A compound having the general formula:

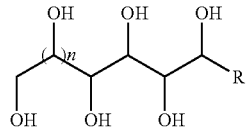

wherein n is 0, 1, or 2; and
R is an alkenyl group having 5 or more carbons.

6. The compound of claim 5, wherein n is 0.
7. The compound of claim 5, wherein n is 1.
8. The compound of claim 5, wherein n is 2.

* * * * *